US00PP19642P2

(12) United States Plant Patent
Heinrich

(10) Patent No.: US PP19,642 P2
(45) Date of Patent: Jan. 20, 2009

(54) ***NEMESIA* PLANT NAMED 'WESNEPA'**

(50) Latin Name: *Nemesia hybrida*
Varietal Denomination: Wesnepa

(75) Inventor: Westhoff Heinrich, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 11/983,736

(22) Filed: Nov. 12, 2007

(51) Int. Cl.
*A01H 5/00* (2006.01)

(52) U.S. Cl. ..... Plt./458
(58) Field of Classification Search ..... Plt./458
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Nemesia* plant named 'Wesnepa', characterized by its compact, upright and uniformly mounded growth habit; freely branching and flowering plant habit; durable dark green-colored leaves; creamy white-colored flowers; and good garden performance.

1 Drawing Sheet

Botanical designation: *Nemesia hybrida.*
Cultivar denomination: 'Wesnepa'.

BACKGROUND OF THE INVENTION

The present invention relates to a new and distinct cultivar of *Nemesia,* botanically known as *Nemesia hybrida* and hereinafter referred to by the name 'Wesnepa'.

The new *Nemesia* is a product of a planned breeding program conducted by the Inventor in Südlohn, Germany. The objective of the breeding program is to create new compact *Nemesia* cultivars with uniform plant habit and attractive flower coloration.

The new *Nemesia* originated from a cross-pollination made by the Inventor in 2004 in Südlohn, Germany of a proprietary selection of *Nemesia hybrida* identified as code number 04P009, not patented, as the female, or seed, parent with a proprietary selection of *Nemesia hybrida* identified as code number 04P180, not patented, as the male, or pollen, parent. The new *Nemesia* was discovered and selected by the Inventor as a single flowering plant within the progeny of the stated cross-pollination in a controlled environment in S üdlohn, Germany in 2005.

Asexual reproduction of the new *Nemesia* by vegetative cuttings in a controlled environment in Südlohn, Germany since 2005, has shown that the unique features of this new *Nemesia* are stable and reproduced true to type in successive generations.

SUMMARY OF THE INVENTION

The cultivar Wesnepa has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Wesnepa'. These characteristics in combination distinguish 'Wesnepa' as a new and distinct cultivar of *Nemesia:*

1. Compact, upright and uniformly mounded growth habit.
2. Freely branching and flowering plant habit.
3. Durable dark green-colored leaves.
4. Creamy white-colored flowers.
5. Good garden performance.

Plants of the new *Nemesia* differ from plants of the female parent selection in the following characteristics:

1. Plants of the new *Nemesia* are more upright than and not as outwardly spreading as plants of the female parent selection.
2. Plants of the new *Nemesia* have longer lateral branches than plants of the female parent selection.
3. Plants of the new *Nemesia* have larger leaves than plants of the female parent selection.

Plants of the new *Nemesia* differ from plants of the male parent selection in the following characteristics:

1. Plants of the new *Nemesia* are shorter than plants of the male parent selection.
2. Plants of the new *Nemesia* have larger leaves than plants of the male parent selection.
3. Plants of the new *Nemesia* have larger and more open flowers than plants of the male parent selection.
4. Plants of the new *Nemesia* and the male parent selection differ in flower color as plants of the male parent selection have white-colored flowers with light blue-colored margins.

Plants of the new *Nemesia* can be compared to plants of the cultivar Intraibana, disclosed in U.S. Plant Pat. No. 17,542. In side-by-side comparisons conducted by the Inventor in Südlohn, Germany, plants of the new *Nemesia* differed from plants of the cultivar Intraibana in the following characteristics:

1. Plants of the new *Nemesia* were more upright than and not as outwardly spreading as plants of the cultivar Intraibana.
2. Plants of the new *Nemesia* had larger and darker green-colored leaves than plants of the cultivar Intraibana.

3. Plants of the new *Nemesia* had larger flowers than plants of the cultivar Intraibana.
4. Plants of the new *Nemesia* and the cultivar Intraibana differed in flower color as plants of the cultivar Intraibana had yellow-colored flowers.

BRIEF DESCRIPTION OF THE PHOTOGRAPH

The accompanying colored photograph illustrates the overall appearance of the new *Nemesia,* showing the colors as true as it is reasonably possible to obtain in colored reproductions of this type. Colors in the photograph may differ slightly from the color values cited in the detailed botanical description which accurately describe the colors of the new *Nemesia.* The photograph comprises a side perspective view of a typical flowering plant of 'Wesnepa' grown in a container.

DETAILED BOTANICAL DESCRIPTION

The aforementioned photograph and following observations, measurements and values describe plants grown in Südlohn, Germany, under commercial practice during the summer in a glass-covered greenhouse with day temperatures ranging from 20° C. to 25° C., night temperatures ranging from 16° C. to 18° C. and light levels ranging from 3,000 lux to 50,000 lux. Rooted young plants were grown for about 20 weeks when the photograph and description were taken. In the following description, color references are made to The Royal Horticultural Society Colour Chart, 2001 Edition, except where general terms of ordinary dictionary significance are used.

Botanical classification: *Nemesia hybrida* cultivar Wesnepa.

Parentage:

*Female, or seed, parent.*—Proprietary selection of *Nemesia hybrida* identified as code number 04P009, not patented.

*Male, or pollen, parent.*—Proprietary selection of *Nemesia hybrida* identified as code number 04P180, not patented.

Propagation:

*Type.*—By vegetative cuttings.

*Time to initiate roots, summer.*—About 10 to 14 days at temperatures of 20° C.

*Time to initiate roots, winter.*—About 16 to 18 days at temperatures of 20° C.

*Time to produce a rooted young plant, summer.*—About 21 to 24 days at temperatures of 20° C.

*Time to produce a rooted young plant, winter.*—About 24 to 26 days at temperatures of 20° C.

*Root description.*—Fibrous; color, close to 158A.

*Rooting habit.*—Freely branching; moderately dense to dense.

Plant description:

*Plant and growth habit.*—Compact, upright and uniformly mounded growth habit; plants roughly spherical. Freely branching with two lateral branches potentially forming at every node. Vigorous growth habit.

*Plant height.*—About 15 cm to 20 cm.

*Plant diameter.*—About 37 cm.

Lateral branch description:

*Length.*—About 16 cm.

*Diameter.*—About 2 mm.

*Internode length.*—About 4.1 cm.

*Strength.*—Strong; flexible.

*Aspect.*—Upright to somewhat outwardly spreading.

*Texture.*—Smooth, glabrous.

*Color.*—146A.

Foliage description:

*Arrangement.*—Opposite, simple; sessile.

*Length.*—About 6.8 cm.

*Width.*—About 2.1 cm.

*Shape.*—Lanceolate.

*Apex.*—Acute.

*Base.*—Attenuate.

*Margin.*—Serrate.

*Texture, upper and lower surfaces.*—Smooth, glabrous.

*Venation pattern.*—Pinnate; arcuate.

*Color.*—Developing foliage, upper surface: 137A. Developing foliage, lower surface: 146B. Fully expanded foliage, upper surface: 147A; venation, 147A. Fully expanded foliage, lower surface: 147B to 147C; venation, close to 147C to 147D.

Flower description:

*Flower arrangement and habit.*—Zygomorphic solitary flowers arranged on terminal racemes; flowering acropetally towards the apex. Flowers bilabiate. Flowers face mostly outwardly. Flowers not persistent. Freely flowering habit with about 21 to 31 flowers and flower buds per raceme.

*Fragrance.*—None detected.

*Natural flowering season.*—In Germany, plants flower from spring to fall; flowering continuous during this period. Flowers last about five to seven days on the plant.

*Flower diameter.*—About 2.95 cm.

*Flower depth.*—About 2.3 cm.

*Throat diameter.*—About 9 mm.

*Tube length.*—About 1 cm.

*Tube diameter, at base of flower.*—About 3.3 mm.

*Flower buds.*—Shape: Ovoid. Length: About 1.1 cm. Diameter: About 6.3 mm. Color: Towards the base, 18A to 18C; towards the apex, 4D; venation, N79C.

*Petals.*—Arrangement: Five modified petals; four upper petals fused forming an upright lobed and arched banner lip; lower petal modified into a larger lip with convex oval protuberance which serves as a pollinator nectar guide and landing platform. Shape: Upper lip: Oblong. Lower lip: Spatulate. Apex: Upper lip: Rounded. Lower lip: Emarginate. Margin: Upper lip: Entire. Lower lip: Slightly undulate. Length: Upper lip: About 1.3 cm. Lower lip: About 1.5 cm. Width: Upper lip: About 6 mm. Lower lip: About 2.4 cm. Texture, upper and lower lips, upper and lower surfaces: Smooth, glabrous. Color, upper and lower lips lobes: When opening, upper surface: Upper lip, 10D; lower lip, 10C to 10D; protuberance, 17A; nectar guides, 79A. When opening, lower surface: 4D; venation, N79C. Fully opened, upper surface: Upper petals, between 4D and 10B; lower petal, between 4D and 10A to 10C; protuberance, 17A; nectar guides, N92B. Color becoming closer to 4D with development. Fully opened, lower surface: 4D; venation, between 79C and N79C. Color, tube: Upper lip, 4D; lower lip, 16D; venation, N79C. Color, throat: Upper lip, 155D; lower lip, N25B; venation, N79B.

*Sepals.*—Arrangement: Calyx star-shaped with five sepals fused at the base. Shape: Acicular. Apex: Acute. Margin: Entire. Length: About 6.6 mm. Width: About 1.3 mm. Texture, upper and lower surfaces: Pubescent. Color, upper and lower surfaces: 146A to 146B.

*Pedicels.*—Length: About 2 cm. Diameter: Less than 1 mm. Strength: Moderately strong; flexible. Texture: Pubescent. Color: 146B.

*Reproductive organs.*—Stamens: Quantity/arrangement: Four per flower. Filament length: About 3.2 mm. Filament color: Close to 155D. Anther shape: Reniform. Anther length: About 1.6 mm. Anther diameter: About 1 mm. Anther color: 11A. Pollen amount: Abundant. Pollen color: 11B. Pistils: Quantity: One per flower. Pistil length: About 3 mm. Style length: Less than 1 mm. Style color: 144A to 144B. Stigma shape: Ovate. Stigma color: 145A. Ovary color: 144A to 144B. Seed/fruit: Seed and fruit development have not been observed on plants of the new *Nemesia.*

Pathogen/pest resistance: Plants of the new *Nemesia* have not been observed to be resistant to pests and pathogens common to *Nemesia.*

Garden performance: Plants of the new *Nemesia* have been observed to tolerate wind and rain and have good garden performance.

Temperature tolerance: Plants of the new *Nemesia* have been observed to tolerate temperatures from about 5° C. to about 30° C.

It is claimed:

1. A new and distinct *Nemesia* plant named 'Wesnepa' as illustrated and described.

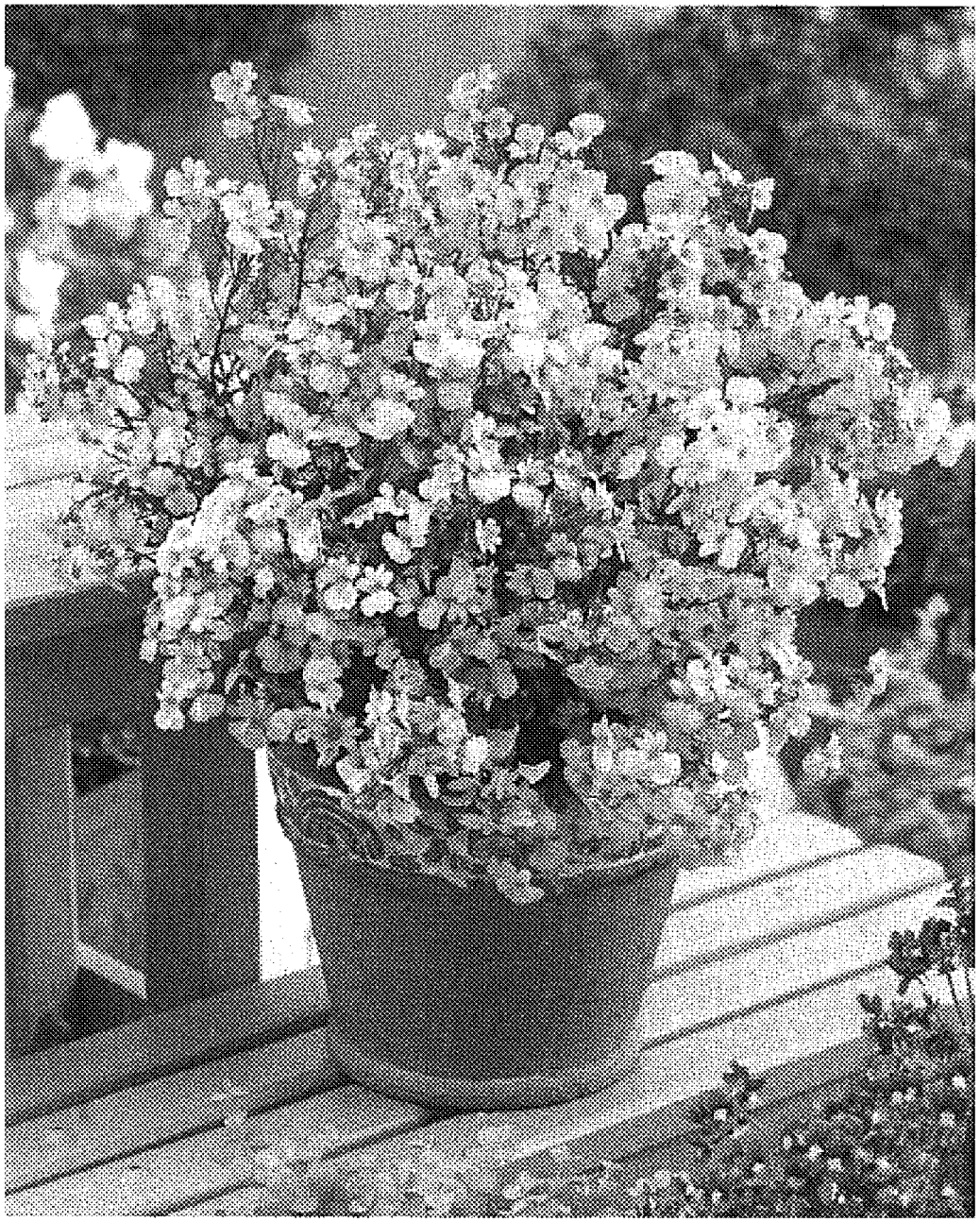

* * * * *